US007559890B2

(12) United States Patent
Wallace et al.

(10) Patent No.: US 7,559,890 B2

(45) Date of Patent: Jul. 14, 2009

(54) ENDOSCOPIC IMAGING OF AN ORGAN SYSTEM

(75) Inventors: Jeffrey M Wallace, Baltimore, MD (US); Santosh Venkatesha, Baltimore, MD (US); Keith Peacock, Columbia, MD (US); Nitish V Thakor, Clarksville, MD (US); Ananth Natarajan, San Marino, CA (US)

(73) Assignee: Ikona Medical Corporation, Marina del Rey, CA (US)

( * ) Notice: Subject to any disclaimer, the term of this patent is extended or adjusted under 35 U.S.C. 154(b) by 268 days.

(21) Appl. No.: 10/785,802

(22) Filed: Feb. 24, 2004

(65) Prior Publication Data

US 2004/0220478 A1 Nov. 4, 2004

Related U.S. Application Data

(60) Provisional application No. 60/450,224, filed on Feb. 26, 2003.

(51) Int. Cl.
*A61B 1/00* (2006.01)
*A61B 1/04* (2006.01)
*A61B 1/06* (2006.01)

(52) U.S. Cl. ........................ 600/129; 600/170; 600/176

(58) Field of Classification Search ................. 600/103, 600/117, 135, 160, 170, 173
See application file for complete search history.

(56) References Cited

U.S. PATENT DOCUMENTS

| | | | | |
|---|---|---|---|---|
| 5,005,559 | A * | 4/1991 | Blanco et al. | 600/114 |
| 5,184,602 | A | 2/1993 | Anapliotis et al. | 128/6 |
| 5,313,306 | A | 5/1994 | Kuban et al. | 348/65 |
| 5,398,670 | A * | 3/1995 | Ortiz et al. | 600/114 |
| 5,764,809 | A * | 6/1998 | Nomami et al. | 382/284 |
| 5,807,237 | A | 9/1998 | Tindel | 600/114 |
| 5,888,193 | A | 3/1999 | Breidenthal et al. | 600/160 |
| 5,961,445 | A * | 10/1999 | Chikama | 600/112 |
| 6,491,645 | B1 * | 12/2002 | Gaber | 600/571 |

(Continued)

FOREIGN PATENT DOCUMENTS

JP 10-318727 * 12/1998

(Continued)

OTHER PUBLICATIONS

Baker et al., "A Theory of Catadioptric Image Formation", Proc. 6$^{th}$ Int'l Conf. on Computer Vision, Bombay, Jan. 1998, pp. 35-42.

(Continued)

*Primary Examiner*—John P Leubecker
*Assistant Examiner*—Philip R Smith
(74) *Attorney, Agent, or Firm*—Kauth, Pomeroy, Peck & Bailey LLP

(57) ABSTRACT

Certain embodiments include an endoscope and methods for imaging using the endoscope. The endoscope may include an imaging channel and a tip positioned at one end of the imaging channel, the tip adapted to collect light from a field of view that extends 360° around at least a portion of the endoscope and to transmit the light to the imaging channel. Certain embodiments may also utilize various sensors, controllers and processing mechanisms to record and process images into a representation, move the endoscope in and out of the endometrial cavity, and to biopsy a portion of the endometrium.

28 Claims, 11 Drawing Sheets

U.S. PATENT DOCUMENTS

| | | | | |
|---|---|---|---|---|
| 6,537,209 | B1 | 3/2003 | Pinkhasik et al. | 600/170 |
| 6,638,216 | B1 | 10/2003 | Durell | 600/173 |
| 6,668,185 | B2 * | 12/2003 | Toida | 600/425 |
| 6,887,196 | B2 * | 5/2005 | Arai et al. | 600/178 |
| 6,921,920 | B2 * | 7/2005 | Kazakevich | 257/81 |
| 6,929,603 | B2 | 8/2005 | Durell | 600/173 |
| 7,110,124 | B2 * | 9/2006 | Jensen et al. | 356/626 |
| 2001/0010555 | A1 * | 8/2001 | Driscoll, Jr. | 348/335 |
| 2002/0052547 | A1 * | 5/2002 | Toida | 600/425 |
| 2003/0191369 | A1 | 10/2003 | Arai et al. | 600/173 |
| 2004/0122327 | A1 * | 6/2004 | Belson et al. | 600/476 |
| 2004/0254424 | A1 | 12/2004 | Simkulet et al. | 600/176 |

FOREIGN PATENT DOCUMENTS

| | | | |
|---|---|---|---|
| JP | 11-174603 | * | 7/1999 |

OTHER PUBLICATIONS

Nayar, "Omnidirectional Video Camera", Proc. DARPA Image Understanding Workshop, New Orleans, May 1997.

Svoboda et al., "Central Panoramic Cameras: Geometry and Design", Center for Machine Perception Czech Technical University Research Report No. K335/97/147, Dec. 5, 1997.

* cited by examiner

ENDOSCOPIC IMAGING OF AN ORGAN SYSTEM

This application claims priority in U.S. provisional patent application No. 60/450,224, filed Feb. 26, 2003.

FIELD OF INVENTION

This present invention relates to methods and devices for imaging and/or biopsy.

BACKGROUND

A common practice in gynecology is for a woman to have an annual examination including speculum and bimanual examination and a Papanicolau smear (which primarily screens for cervical cancer). On the other hand, there is no current screening test for endometrial cancer, the most prevalent form of gynecological cancer. Therefore imaging and biopsy is usually delayed until after symptoms develop. Patients with endometrial carcinoma or hyperplasia typically exhibit increased or irregular menses or postmenopausal vaginal bleeding (PMB). The standard of care as recommended by the American College of Obstetricians and Gynecologists is for patients with these symptoms to undergo office-based endometrial biopsy (EMB) and endocervical curettage (ECC). The EMB is a blind biopsy done typically with an endometrial Pipelle™. The Pipelle™ is a disposable plastic tube measuring approximately 3.1 mm in diameter with an internal plunger which is drawn back to create a small amount of suction once the device has been introduced into the endometrial cavity via the cervix. By moving the device in and out, a sample of endometrial tissue is removed for histologic examination.

None of the above techniques use imaging of the endometrium. There are currently two imaging modalities that are available. The first is transvaginal ultrasound, which may be useful in screening patients with PMB for endometrial cancer. The other technique for imaging the endometrium is hysteroscopy. Not surprisingly, using the hysteroscope for image-guided biopsy has been shown to be superior to the above blind procedures. However, the majority of gynecologists do not perform hysteroscopy. In addition to the issues of pain, invasiveness, and morbidity, there is a steep learning curve. In addition, the use of a distending media, for example, saline or a gas (e.g., $CO_2$) to create open space in the uterus, may lead to problems. In addition, because the hysteroscope can only image the tissue in front of it, experience and manual dexterity are required in order to examine the whole endometrium.

SUMMARY

Certain embodiments of the invention relate to methods and devices used for imaging a body system, including the endometrial cavity.

One embodiment relates to methods for imaging an endometrial cavity, including positioning an endoscope at least partially within the endometrial cavity, and imaging tissue within the endometrial cavity around a circumference of at least a portion of the endoscope.

In one aspect of certain related embodiments, a method as described above may also include obtaining a plurality of images of the endometrial cavity by moving the endoscope through at least a portion of the endometrial cavity and imaging tissue around the circumference of at least a portion of the endoscope at a plurality of positions within the endometrial cavity. Such a method may also include storing the plurality of images, and processing the images with an image data processing system to create at least one representation of at least a portion of the endometrial cavity.

Certain embodiments also relate to a method including positioning at least a portion of an endoscope within the endometrial cavity, obtaining an image of tissue in the endometrial cavity extending 360 degrees around at least a portion of the endoscope, and moving the endoscope within the endometrial cavity to obtain a plurality of images each extending 360 degrees around at least a portion of the endoscope.

In one aspect of certain related embodiments, a method such as that described above may further include determining an area of interest based on the images. In addition, such a method may also include performing a biopsy in the area of interest based on the images.

BRIEF DESCRIPTION OF THE DRAWINGS

Certain embodiments of the invention are described with reference to the accompanying drawings, which, for illustrative purposes, are not necessarily drawn to scale.

DETAILED DESCRIPTION

Certain embodiments of the present invention pertain to minimally invasive imaging and biopsy systems and methods used to identify pathology of an organ system such as the uterus. In one preferred application/embodiment, endometrial imaging is described. The endometrial cavity may be defined as the endometrial lining and/or any pathology detectable from the surface of the endometrium within the uterus. Imaging may be defined as collecting electromagnetic rays and creating at least a two dimensional representation of an object. Certain embodiments include an omni-directional (360-degree) viewing endoscope controlled by a position sensor mechanism to produce images of the endometrial cavity for visualization of tissue and pathology that is detectable within the cavity. Certain embodiments may also include imaging devices such as, for example, full color CCD, spectral multi-wavelength (including visible, infrared, and ultraviolet, imaging technology, or other electrical transducer to produce a detailed visual map of the endometrial cavity in order to assist the clinician in identifying uterine pathologies.

Certain embodiments of the present invention also integrate an apparatus for directed biopsy, accomplished using a position sensor system. Using position tracking, the coordinates of the area of interest from imaging system can be translated back to the physical location within the endometrial cavity. Such embodiments augment conventional biopsy with a detailed 360 degree, omni-directional view of the endometrial cavity around the endoscope, thereby decreasing the need for manual dexterity. Such embodiments may be used as a minimally invasive tool for identification and directed biopsy of uterine or other organ pathology.

As noted above, certain embodiments of the invention relate to methods and apparatus for imaging and sampling tissue from the endometrial cavity.

Figure 1:
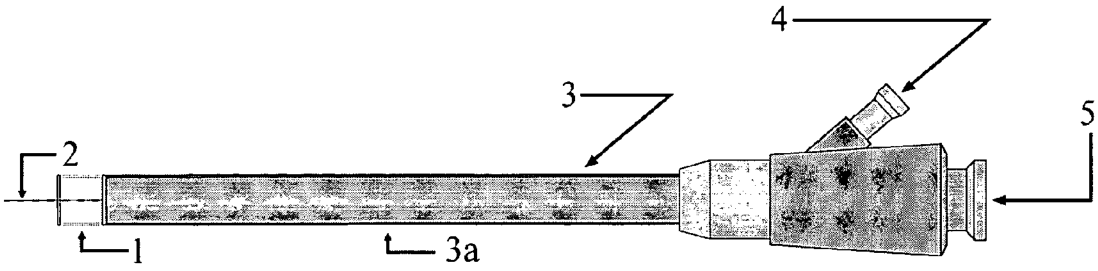
FIG. 1 is a schematic of an embodiment of an imaging apparatus that allows for omni-directional viewing. Light is collected at the omni-directional tip (1) and is transferred to the imaging channel (5) with the appropriate detector.

In accordance with certain embodiments, in order to image the tissue within the endometrial cavity (or organ cavity), a specialized endoscope is used. As seen in the embodiment illustrated in FIG. 1, an imaging apparatus includes a rigid or flexible endoscope (3), an illumination channel (4), and an imaging channel (5). A camera, electrical transducer or other imaging technology may be attached to the imaging channel (5) to capture images. The endoscope contains a body portion (3*a*) that surrounds at least a portion of the imaging channel of the device. One aspect of the imaging apparatus is the omni-directional tip (1) that will allow it to visualize 360 degrees of the endometrial cavity perpendicular or near perpendicular to the optical axis (2) at a position in the endometrium at or adjacent to the tip. The omni-directional tip may also be positioned a distance away from an end region of the endoscope. The endoscope is preferably positioned transcervically to the uterine fundus. As the apparatus is introduced or retracted, images of the endometrial cavity can be captured as the tip of the scope passes through the cavity.

Figure 2:
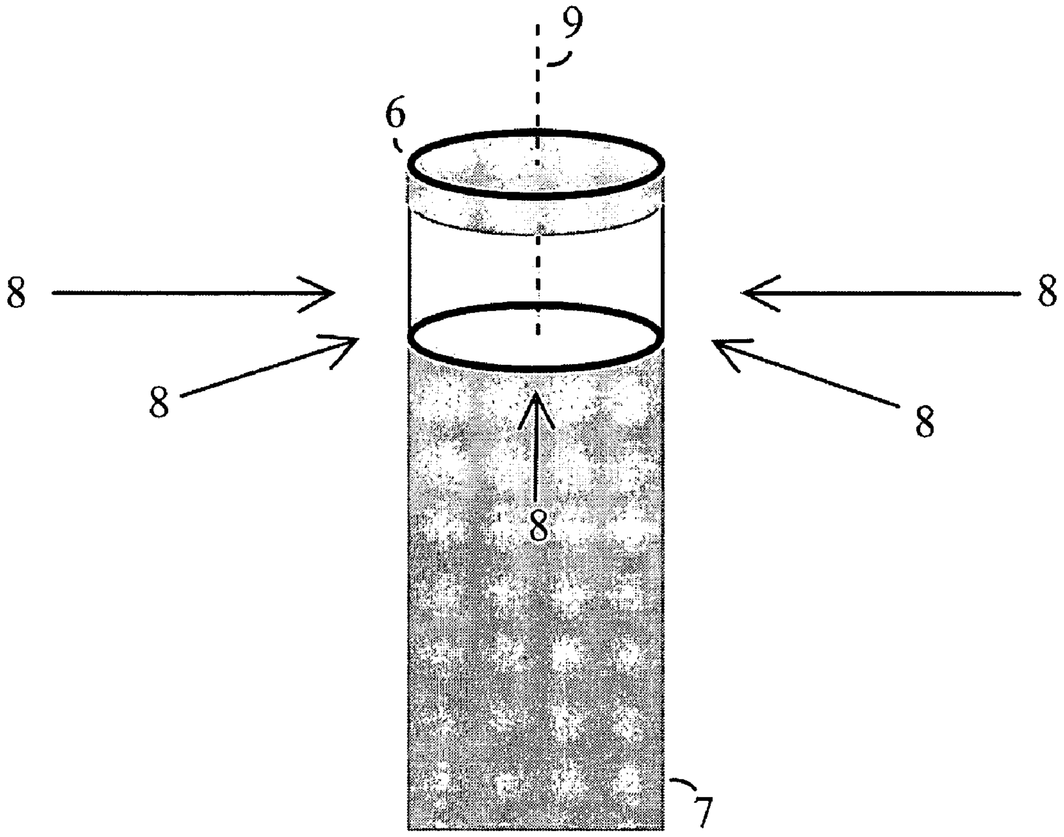
FIG. 2 is an illustration of an embodiment of an omni-directional tip (6) collecting light from all directions. Light (8) entering the tip will be transferred into the endoscope body portion (7).

As seen in FIG. 2, any light (8) collected at the omni-directional tip (6) will be imaged into the endoscope body portion (7) and transferred to an imaging sensor on the other end of the endoscope. To illuminate the field of view, fiber optics may be used. Fiber optic light conductors may be mounted coaxially around the image channel of the endoscope, much like standard endoscopes. This allows for transmission of light from an illumination channel (see FIG. 1 illumination channel 4) to the omni-directional tip, where the light can be directed to the field of view and therefore illuminate the tissue that will be imaged. Unlike some conventional imaging methods in which imaging is done in front of the endoscope tip with a limited field of view using liquid or gas distention, (as done in conventional hysteroscopy and related imaging), certain embodiments image the endometrial cavity coapted 360 degrees around the tip, perpendicular or near perpendicular to the optical axis (2). Such device will capture the images of tissue and collect a panoramic view (360 degree view). When the endoscope is retracted/inserted through the cavity, as described below (FIG. 8), the successive views that are formed can be combined into a collage of all the images. Therefore a full image of all the views can be combined displaying the entire length of the endometrial cavity.

Figure 3:
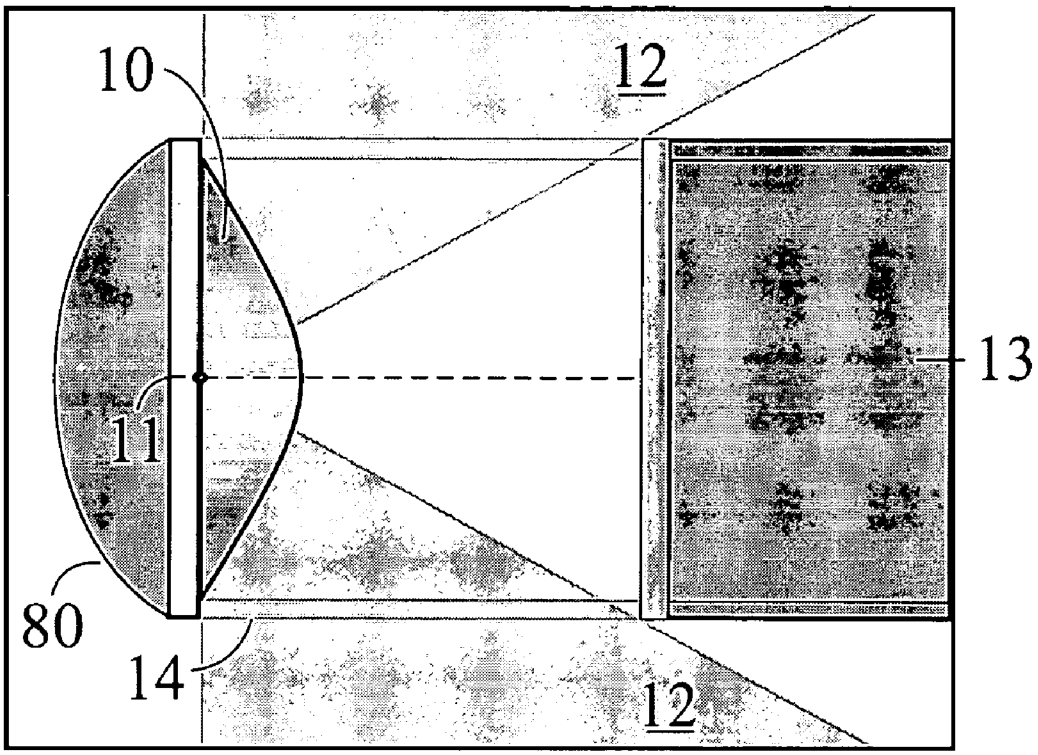
FIG. 3 is a schematic of an embodiment of an omni-directional tip. Using a reflecting medium, such as a mirror, the light within the displayed field of view (12) aimed at the perspective point (11) will be reflected off of the tip (10) and imaged through the endoscope (13).
Figure 4:
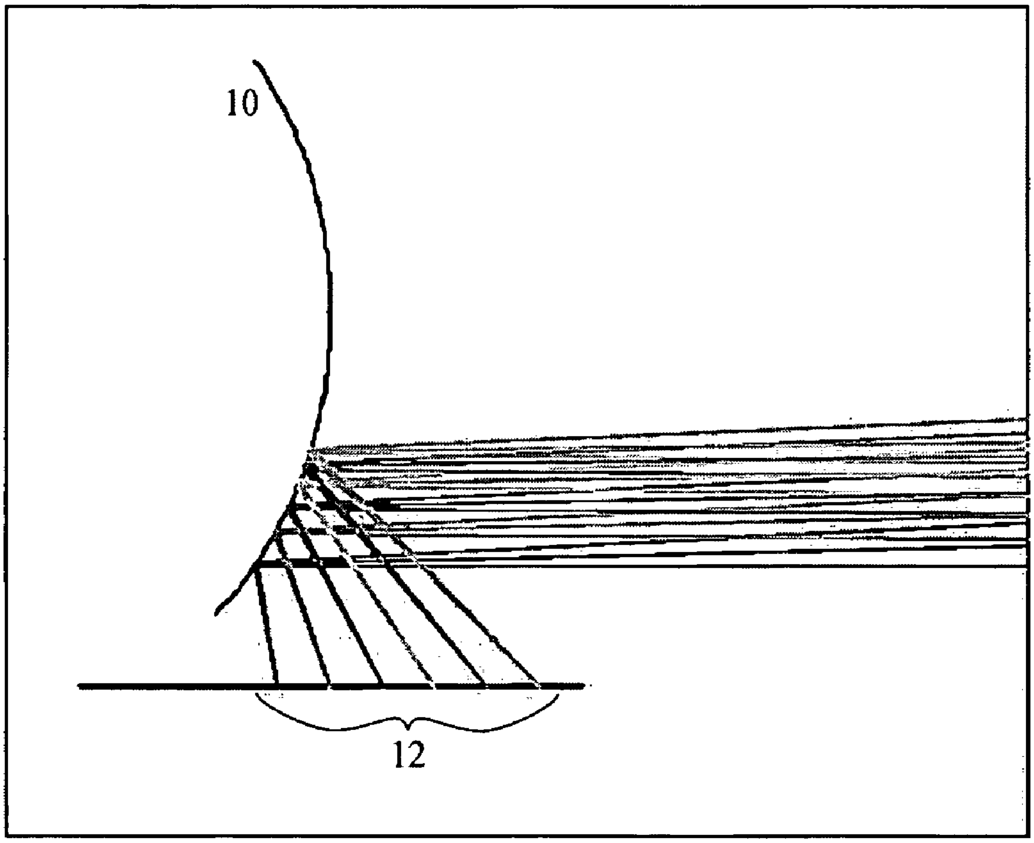
FIG. 4 illustrates how light is reflected off a reflective surface in the field of view in accordance with an embodiment of the present invention. Any object within the field of view (12) will project light off the mirror or other reflective surface (10) into the image transfer optics of the endoscope.

The ability of the imaging apparatus to capture light from 360 degrees at the omni-directional tip is illustrated in multiple embodiments. FIG. 3 shows a schematic of one embodiment of an omni-directional tip. This method includes an omni-directional tip that uses a reflective element (10), such as a mirror to image the surrounding tissue. The shape of the reflective element used in this embodiment can vary depending on the subsequent image processing that will be used to un-warp the collected image. Any light within the field of view (12) that can create an image will pass through a window (14) on the tip. The window (14) may preferably made from a clear material such as plastic, acrylic, glass or some other clear substance. The image is reflected into the endoscope body portion (13) to be imaged by a sensor at the imaging mount of the endoscope (See imaging mount 5 in FIG. 1). An optional element can be attached to the tip of the endoscope. An example of such an element is an end cap structure (80). The end cap structure may take a variety of shapes, for example a convex shape such as that shown in end cap (80) in FIG. 3. Such an end cap may facilitate insertion and removal of the endoscope. Through this embodiment, the imaging tip will collect images of tissue that are within the field of view (12)—tissue which is 90 degrees with respect to the optical axis, and further behind the tip. FIG. 4 illustrates the embodiment further. Any light originating within the endoscope's field of view (12), will be reflected off the reflective element (10), and transferred through the endoscope to the imaging detector.

Figure 5:
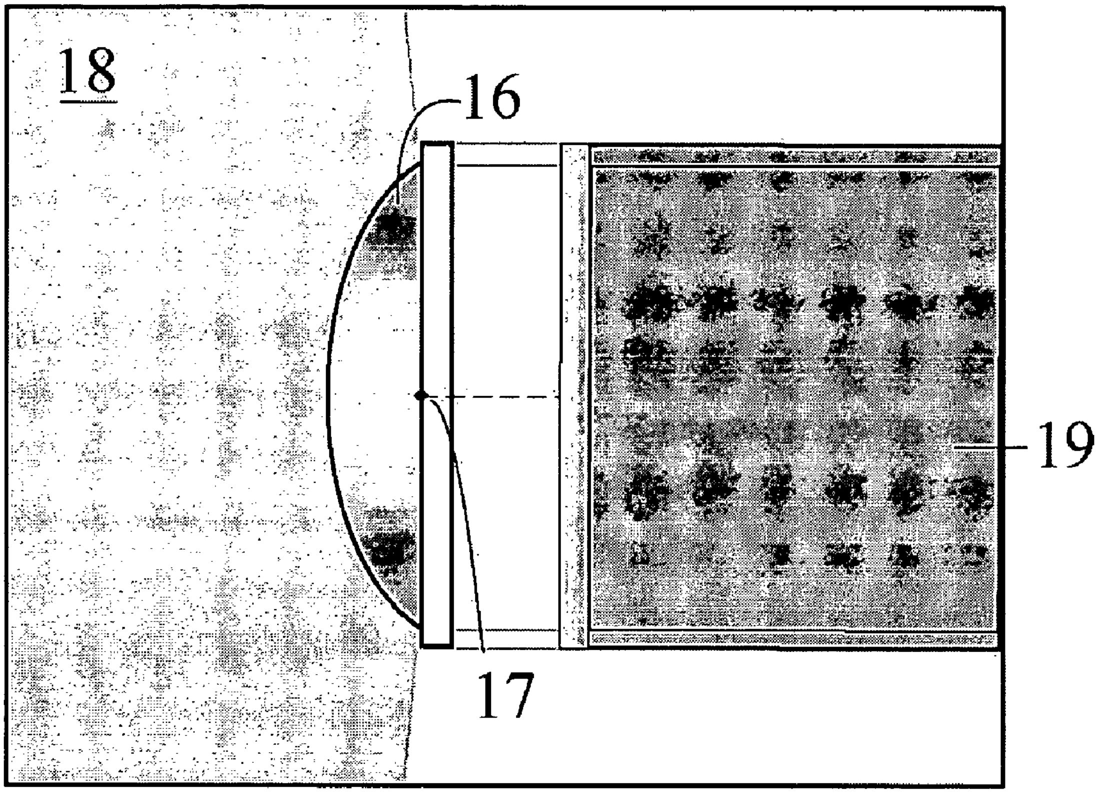
FIG. 5 is a schematic of another embodiment of an omni-directional tip. By refracting the light through the use of a lens element (16), light within the field of view (18) aimed at the perspective point (17) is captured into the endoscope (19).

Another embodiment of an omni-directional tip is shown in FIG. 5. Instead of a reflective element as before, this embodiment uses a lens or a system of lenses (16) to refract the light into the endoscope. All the light that can form an image within the field of view (18) will be refracted into the endoscope body portion (19) and transferred to the imaging sensor at the imaging mount of the endoscope. Using a lens element (16), this embodiment captures images of tissue within the field of view (18) that differs from the field of view (12) in the embodiment illustrated in FIGS. 3 & 4. In the embodiment illustrated in FIG. 5, the field of view (18) includes tissue that is in front and tissue that is oriented up to 90 degrees with respect to the optical axis. As seen in the embodiments in FIGS. 3 and 5, at least a portion of the field of view ((12) in FIG. 3 and (18) in FIG. 5) extends around a circumference of a portion of the endoscope and thus an image including tissue extending around a circumference of the endoscope may be obtained.

Figure 6:
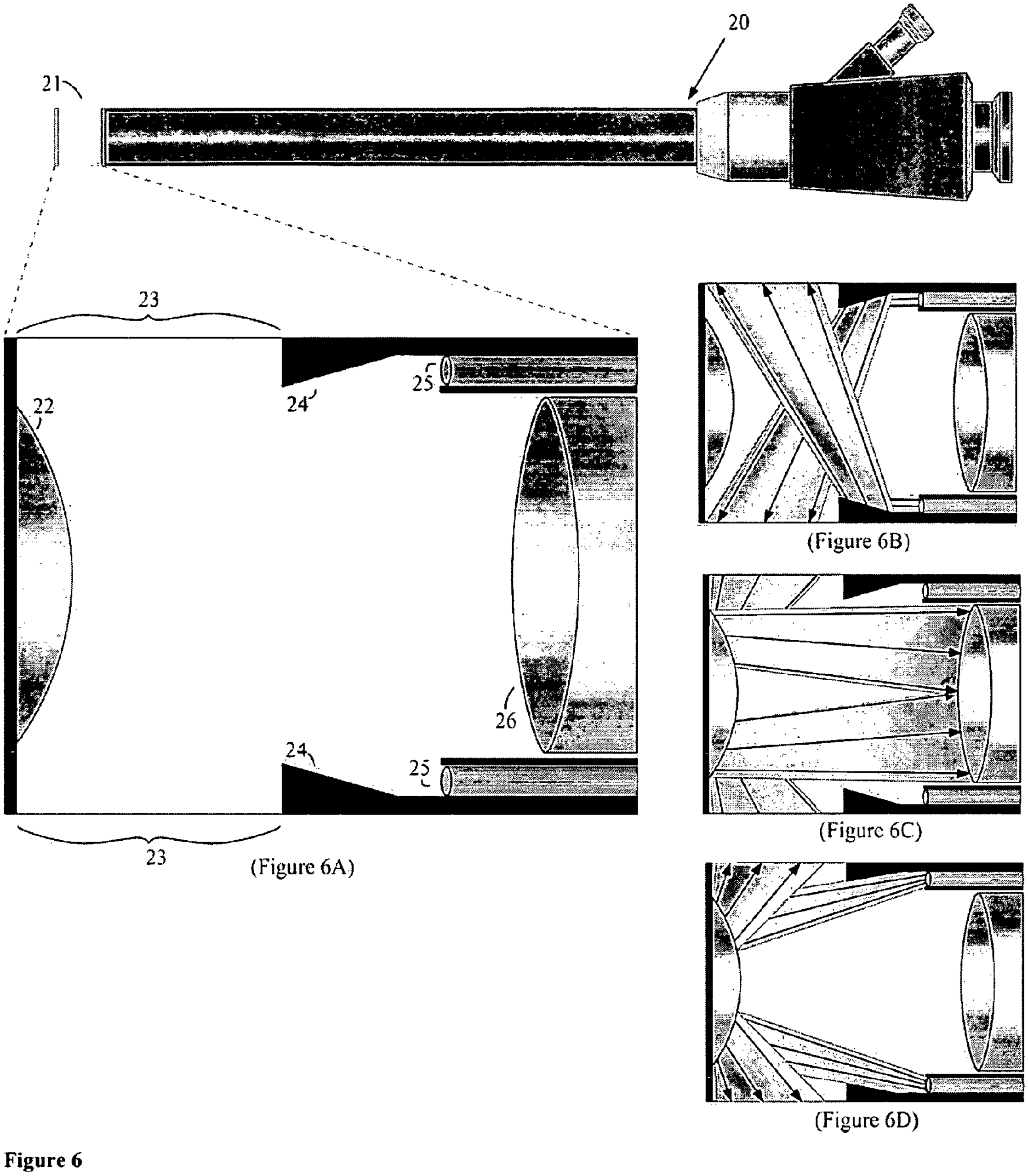
FIGS. 6(*a*)-(*d*) illustrate embodiments of an illumination system in coordination with a reflective element imaging system.

By combining the omni-directional tip with a method for illuminating the field of view from the illumination brought in by the fiber optics mounted coaxially around the endoscope, an embodiment of the imaging system can be established. FIG. 6 illustrates an embodiment of the invention using a reflective element to illuminate the field and a reflective element to image the field. This embodiment includes a more detailed view of an omni-directional tip (21) including a reflective element (22) similar to the reflective element (10) illustrated in FIG. 3. Looking at a cross section of the endoscope's (20) omni-directional tip (21) and region adjacent thereto in the blown up portion of FIG. 6, this embodiment uses fiber optics (25) that are mounted coaxially around imaging optics (26) to illuminate the field of view (23). Light passing through the fiber optics (25), will reflect off a reflecting element, such as a mirror (24) to illuminate the field of view (23) by crossing the optical axis, as illustrated in FIG. 6(*b*), which shows a general schematic of this embodiment illustrating a methodology of illuminating the field of view (23). In parallel with this, as illustrated in FIG. 6(*c*), the imaging system collects light (indicated by lines and arrows) from the field of view (23) and delivers the light towards the endoscope optics (26). An alternate embodiment of the system is shown in FIG. 6D. This embodiment uses the illumination coming from the coaxial fiber optics (25) and reflects the light off the imaging mirror (22) to illuminate the field of view (23). In both embodiments, through the use of the endoscope optics (26), the image is transferred to a detector connected at the end of the imaging channel (5). Nonuniform illumination that may be caused by fiber optic illuminators that are mounted coaxially around the endoscope is corrected subsequently by software once the image acquisition has been completed.

Figure 7:
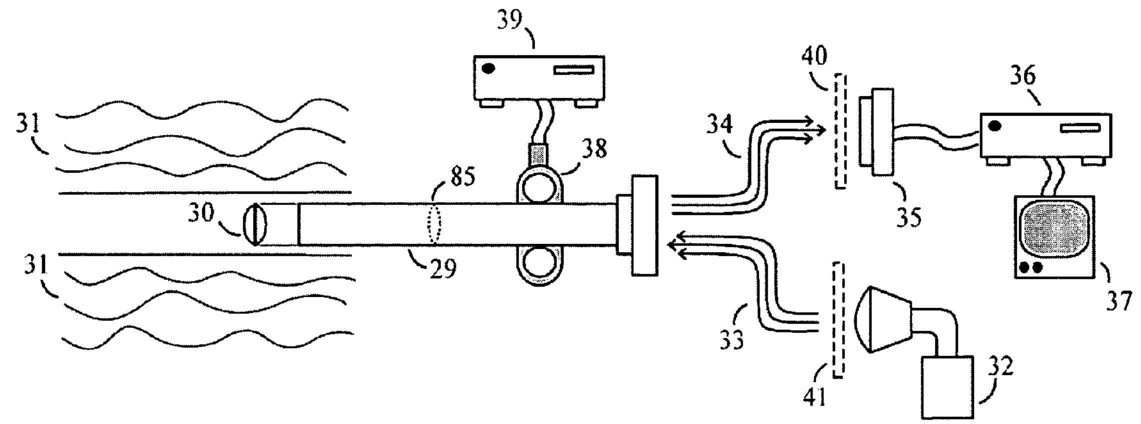
FIG. 7 shows an illustration of how an embodiment of the apparatus may capture images of the endometrial cavity. The endoscope (29) is attached to a position sensor (38). By changing the position of the endoscope, with the position sensor, the imager (35) will be exposed to different areas of the endometrial cavity (31). Through this means, in a systematic fashion, all areas along the length of the cavity may be captured.

An example of the operation of an imaging apparatus in accordance with a preferred embodiment of the present invention is demonstrated in FIG. 7. A systematic method for tracking the position of the endoscope tip is used in this embodiment. This can be accomplished by a position sensor. The position sensor (38) and the controller (39) will control or track the position of the preferably rigid endoscope body portion (29) with the omni-directional tip (30) in order to capture information from endometrial cavity (31). Therefore, as each image is captured in order to use each image to describe a portion of the endometrium, the physical location of the tissue imaged in each capture will be monitored. The omni-directional viewing tip (30) is positioned to image the tissue. Illumination generated by a light source (32) is inputted into the apparatus's illumination channel (33) on the endoscope. The illumination travels through the endoscope and illuminate the field of view through either the omni-directional tip (30) or another reflective or refractive element. The light reflects off the endometrial cavity (31) that is surrounding the tip and be collected back into the endoscope's imaging channel (34) through use of the omni-directional tip. The output of the imaging channel (34) travels to the imaging sensor (35) that is mounted on the endoscope. Digital images of the light is captured with the use of the imaging sensor (35) and computer (36) and its relevant image acquisition. The images that are captured are stored on the computer (36) for processing and displayed on a monitor (37) for observation by the user after the processing is complete. Embodiments may also include one or more lenses (85) positioned at various locations within the body portion (29) of the endoscope.

By positioning filtering elements within the optical path of the embodiment, specific wavelengths of light are imaged. Through the use of wavelength specific imaging, functional information about tissue physiology can be captured. A number of embodiments of this are shown within FIG. 7. A first method can be visualized by placing a filtering element at position (41) where the illumination light is limited to a specific bandwidth determined by the filtering element. Therefore all the light that illuminates the field of view is filtered and the light that is imaged through the imaging channel (34) is of specific wavelengths. A second method can be accomplished if a filtering element is placed at location (40). The tissue is illuminated with broadband light from the light source (32), and the light coming back through the imaging channel (34) is not limited. However, the filtering element at position (40) filters the light just before it is imaged by the imager (35). Therefore, only light of a particular wavelength is captured. Using either method, the filtering element allows for selective imaging of light. In addition, certain embodiments may utilize filters at both locations 40 and 41 or even at different locations if desired. By selecting the correct filter characteristics and location(s), any light, whether in the ultra-violet, visible or infrared spectrum, can be imaged.

Figure 8:
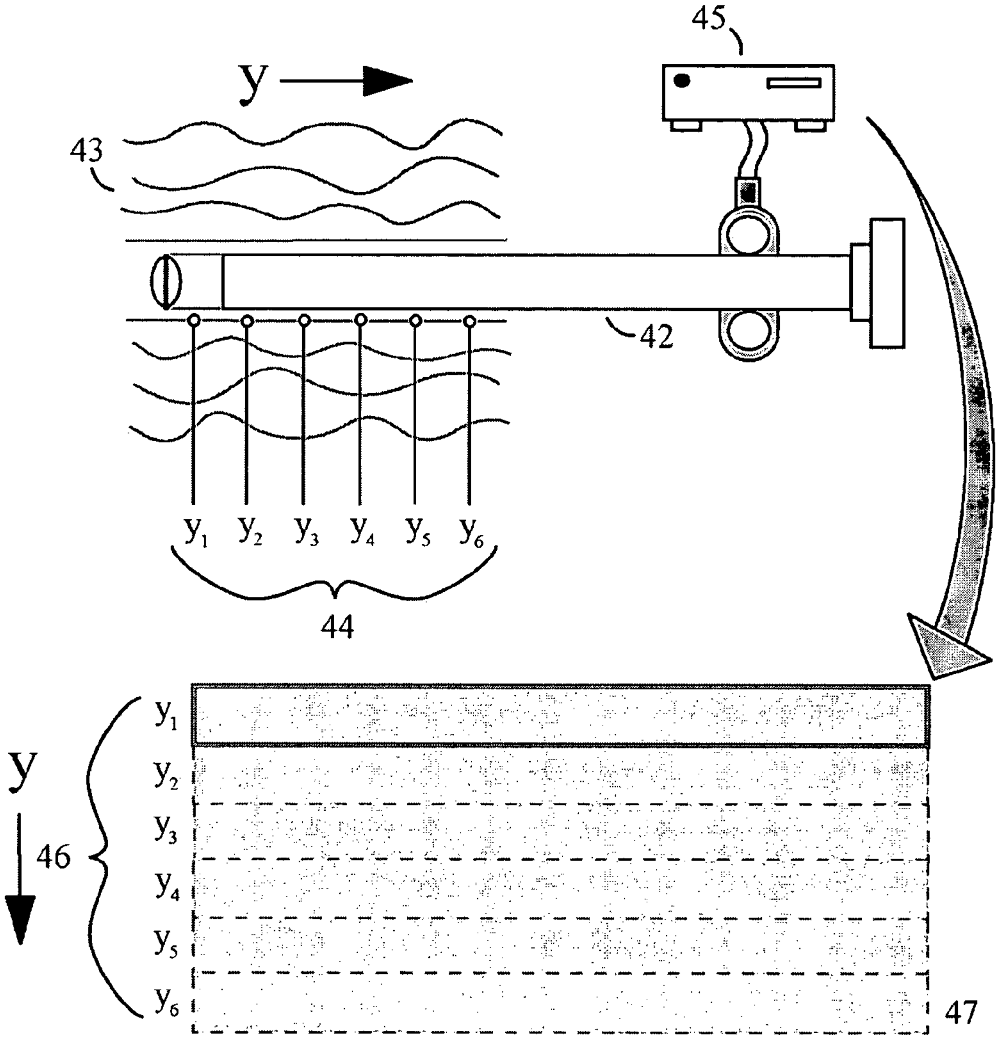
FIG. 8 shows a preferred embodiment of an image collection process. The endoscope (42) will transverse through the endometrial cavity (43) through several positions (44). Through the use of the position sensor setup (45), the positions within the endometrial cavity (43) will correspond to segments (46) of the complete single endometrial map (47).

FIG. 8 illustrates a method embodiment for imaging the entire endometrial cavity using the endoscope such as that illustrated in FIG. 7. Once the endoscope tip (30) is in position within the endometrial cavity (31), it can begin image acquisition. After an image is captured at one location, through the use of the position sensor (38) and controller (39), the endoscope tip (30) will be repositioned to the next position within the cavity. An image is captured at the new location and the endoscope is moved again. As the endoscope tip (30) moves through all the positions $y_1$, $y_2$, . . . (44), it will capture all the images in series. Once all images have been captured, the image acquisition computer will perform image processing on the collected images to generate a single 2-dimensional map of the imaged region (47). The positioning sensor system (45) keeps track of all positions that the imaging apparatus acquired and maintains a single coordinate system for the 2-dimensional map. This allows the position sensor to translate any position (46) on the 2-dimensional map to a position (44) within the endometrial cavity (43). This allows a user the ability to select an area of concern and then return to that location for biopsy.

Figure 9:
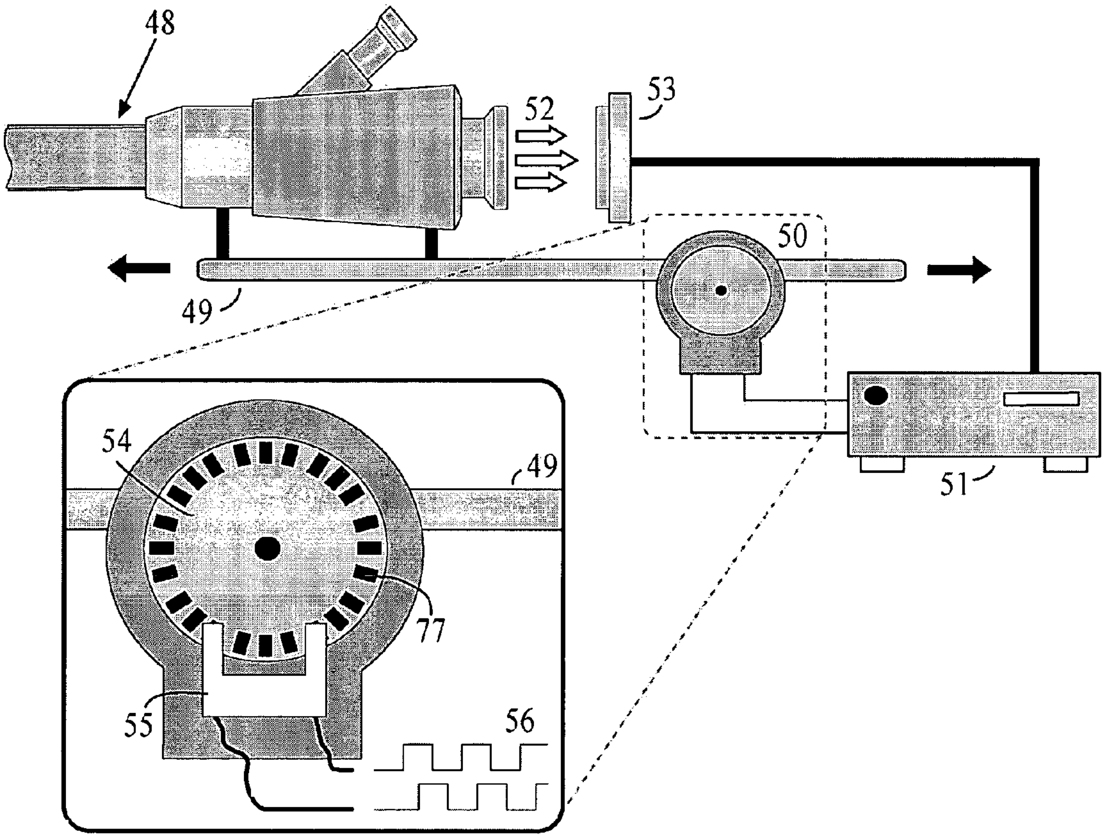
FIG. 9 shows a preferred embodiment of a position sensor apparatus. The endoscope (48) is attached to a linear track (49) with a bi-directional optical encoder (50). As the endoscope moves along the track, the optical encoder will detect changes in position. Therefore the position sensor controller (51) will know at what position the endoscope is at and trigger the detector (53) when the endoscope is at an established location.

A position sensor may synchronize with an imaging sensor such that images are captured at specific positions. This allows for fixed intervals between each image acquisition. One embodiment of an apparatus is shown and described in FIG. 9. FIG. 9 illustrates an endoscope (48) mounted on a linear track (49) so that it can be inserted and retracted along a single axis of motion. The motion of the endoscope (48) in either direction on the track is detected through an optical encoder (50) that is part of the embodiment. This optical encoder (50) is preferably bi-directional. The optical encoder (50) which is used with servomotors and robotic actuators, is able to detect changes in position. The optical encoder (50) is comprised of a round disk (54) with a number of holes (77) extending close to and around the outside edge of the disk and a pair of photo-diode detectors (55). As the endoscope moves along the track, the disk is spun by the motion. The pair of photo-diode detectors are mounted such that the disk (54) blocks the space between the diode and detector. When one of the holes (77) in the disk lines up with the photo-diode detector (55), the detector is able to detect the light from the photo-diode and outputs a signal. As the wheel turns, a pulse pattern is outputted (56) from the photo-diode detector that corresponds to the passing of each of the holes (77) in the disk. The holes (77) are preferably evenly distributed on the disk. As there are a known number of holes, the total distance that the wheel moved can be determined—which indicates the distance the endoscope moved. By using two of these photo-diode detectors, the sensor is able to detect the direction of the motion as well.

The position sensor controller (51) illustrated in FIG. 9 detects these changes from the signals that it is receiving from the optical encoder (56). Through this information, the controller has an accurate measure of any distance the endoscope traveled along the track. This allows the controller to trigger the detector (53) to capture the light (52) that is being imaged by the endoscope. This embodiment allows the device to know exactly how far apart each image in an image series was captured. Additionally, this allows the controller to set the position interval between each image captured.

The image series captured through the use of the apparatus contains visual distortions because of the omni-directional tip (either because of the mirror or the lens system). Each of the images has a characteristic 'fish-eye' distortion that needs to be corrected. Given that the distortion in the images is created by a known source (the lens or mirror at the endoscope tip), the distortion can be removed through software and image processing. This allows the device to collect together undistorted segments of the tissue and combines them into a single 2-dimentional map. This processing is accomplished through software after the image series has been acquired.

Figure 10:
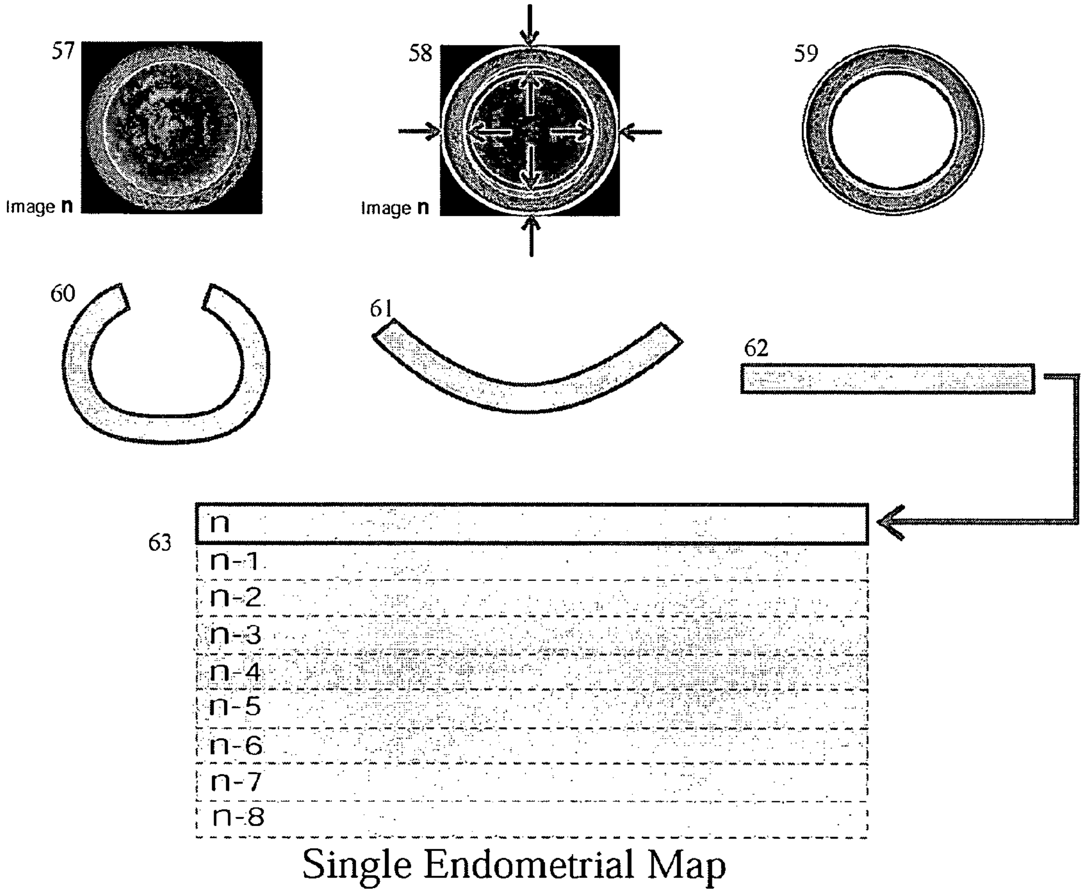
FIG. 10 shows an illustration of how an embodiment of the apparatus may process the images. The omni-directional image (57) is dewarped (60 to 62) and used to generate a single endometrial map (63).

FIG. 10 illustrates an example of the concept of dewarping the series of images. A single image (57) may contain 'fish-eye' distortion because of the shape of the omni-directional viewing tip. In order to unwarp the image, a ring-like segment of the image is selected centered at the vanishing point in the middle of the image (58). The size or thickness of this ring is dependant on the distance the endoscope tip was moved between successive images and the resolution of the images.

Once the ring segment has been identified, the ring segment (59) is clipped out of the overall image for dewarping. Using a transformation based on the shape of the omni-directional viewing tip, the segment can be dewarped through steps (60, 61, 62) into a standard rectangular form (62). However, given that the thickness of the ring segment will preferably be small (in order to maintain high resolution in the endometrial map), in most embodiments, several segments from successive images (n, n-1, n-2, . . . ) will need to be combined or stacked together to form an overall single map (63). Therefore, as the image processing moves through the series of images, visual information about endometrial cavity is segmented out and the final endometrial map is built segment by segment. By taking advantage of the position sensor system (such as that illustrated in FIG. 8) and stacking the image segments one next to another (63), the apparatus is able to create an anatomically scale stack of ring segments (59). Therefore, the 'stacked' image contains anatomical information without the image warping seen in the initial image (57). Once through all the images in the image segment, a complete map has been generated, displaying the visual information that the apparatus collected in its procedure. The map may be of use to the physician, as it allows the user to see within the endometrial cavity or organ cavity and examine the tissue lining for areas of concern, polyps or other pathology.

Figure 11:
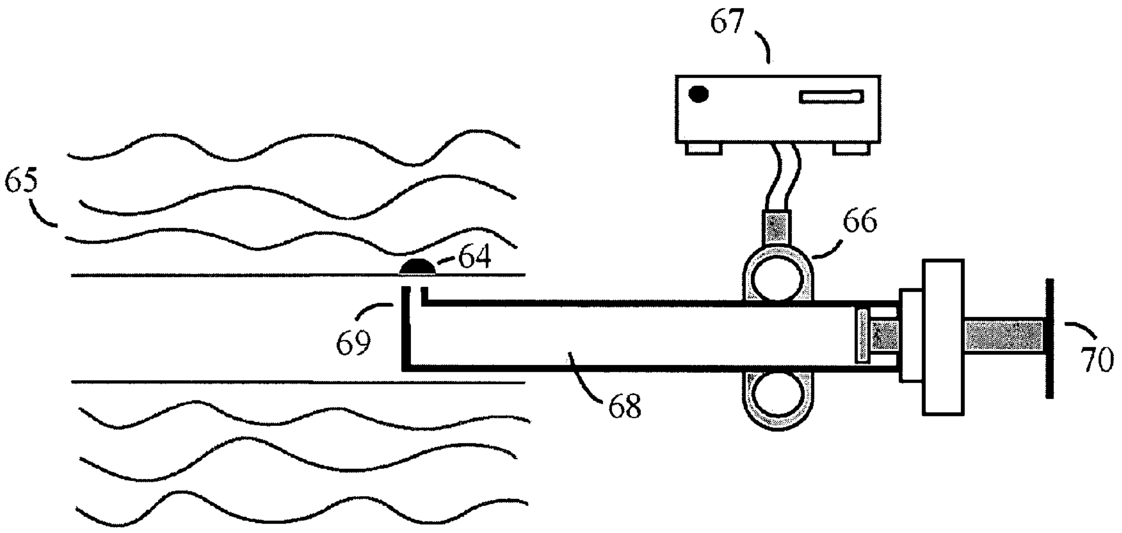
FIG. 11 shows an embodiment of a biopsy apparatus. Once an area of tissue has been identified by a clinician as being of concern (64), the same position sensory system (66,67) can be used to position the biopsy apparatus to the area (64). Tissue samples will be gathered with the collector apparatus (69). Suction created by pulling the plunger back (70) will pull the tissue samples into the cylindrical lumen (68) within the device for histologic testing.

In another aspect of certain embodiments, a biopsy apparatus has the ability to be used in conjunction with the imaging apparatus. The technique for biopsy, whether it is performed through optical means (spectroscopy, optical coherence tomography, etc), or physical means, can be accomplished. An embodiment of physical biopsy is shown in FIG. 11. Once a clinician has identified an area of tissue, that area of concern (64) may be biopsied. Once the area of concern (64) in the region (65) has been identified through the use of the imaging apparatus, a positioning sensor system (66,67) is able to use the same coordinate system used in the image processing algorithms and allow for the positioning of the biopsy apparatus over the area of concern (64). The embodiment uses the position sensor (66) and positioning controller (67) to position a collecting tip (69) at the area of concern (64). The tissue is scraped using the collection tip (69) to obtain a tissue sample. Suction is created within a cylindrical lumen (68) inside of the apparatus through the use of a plunger on the other end (70). The suction draws the sampled tissue into the lumen (68), where it is stored until the apparatus is retracted out of the body and the tissue can undergo histological analysis. Other methods for obtaining biopsy samples may also be utilized.

As set forth above, certain embodiments use and/or relate to an endoscope including an imaging channel and a tip positioned at one end of the imaging channel, the tip adapted to collect light from a field of view that extends 360° around at least a portion of the endoscope and to transmit the light to the imaging channel. Certain embodiments may also utilize various sensors, controllers and processing mechanisms to record and process images into a representation, move the endoscope in and out of the endometrial cavity, and to biopsy a portion of the endometrium. Other aspects and features described above may also be used in certain embodiments.

It is, of course, understood that modifications of the present invention, in its various aspects, will be apparent to those skilled in the art. Additional embodiments are possible, their specific features depending upon the particular application. For example, other data processing and representational methods (for example, a three dimensional representation) may be used instead of or in addition to those discussed above. In addition, certain embodiments may be applicable to other organ systems in addition to the endometrium, including, for example, the gastrointestinal tract.

What is claimed is:

1. A method of investigating uterine pathologies using a map of the endometrial lining of an uninsufflated uterus of a patient, comprising:

attaching an image sensor to an imaging channel contained within a body portion of an endoscope, where the imaging channel connects to an omni-directional tip located at the end of the body portion of the endoscope and possessing optics that enable the image sensor to image endometrial lining coapted around the circumference of the omni-directional tip;

inserting the body portion of the endoscope into the collapsed cavity formed by the uninsufflated uterus of the patient;

moving a portion of the endoscope that is outside the patient's body to move the omni-directional tip of the endoscope around the collapsed cavity formed by the uninsufflated uterus of the patient;

obtaining a series of images of the portions of the endometrial lining that coapt around the circumference of the omni-directional tip of the endoscope as the omni-directional tip moves around the collapsed cavity formed by the uninsufflated uterus of the patient;

processing the series of images to remove at least a portion of the distortion in the images introduced by the omni-directional tip and the endoscope; and combining at least a portion of the processed images into at least one map of the endometrial lining of the uterus of the patient.

2. A method as in claim 1, wherein:

processing the series of images comprises selecting a ring-like segment from one of the images and applying a transformation to convert the ring-like segment into a first rectangular segment, and selecting a ring like segment from a second of the images and applying a transformation to convert the ring-like segment into a second rectangular segment; and combining at least a portion of the processed images comprises combining the first rectangular segment and the second rectangular segment.

3. A method as in claim 1, wherein the field of view of the endoscope extends 360 degrees around at least a portion of the endoscope.

4. A method as in claim 1, wherein the endoscope includes at least one of a reflective element and a refractive element.

5. A method as in claim 1, further comprising obtaining images using a specific wavelength or a specific bandwidth of light.

6. A method as in claim 1, further comprising obtaining images using at least one of visible, ultra-violet and infrared wavelength light.

7. A method as in claim 1, further comprising obtaining images using at least one of reflected imaging, scattered light imaging and florescence imaging of the organ system.

8. A method as in claim 1, further comprising a control system adapted to move the endoscope in the organ system, the control system also adapted to measure the change in position of the endoscope as it moves.

9. A method as in claim 1, further comprising illuminating the organ system with broadband light and recording the images with an image sensor positioned outside of the organ system.

10. A method as in claim 9, wherein the image sensor includes a CCD.

11. A method as in claim 1, further comprising illuminating the organ system with light of a particular wavelength or a particular band of wavelengths and recording the images with an image sensor positioned outside of the organ system.

12. A method as in claim 1, further comprising a control system adapted to position the endoscope to a desired location within the organ system based on the map of the endometrial lining of the uterus of the patient.

13. A method as in claim 1, further comprising capturing images using an image sensor positioned within the organ system and transmitting the images to a device positioned outside of the organ system.

14. A method as in claim 13, wherein the image sensor comprises an electrical transducer.

15. A method as in claim 1, further comprising providing a control system to locate a specific area of interest in the endometrial lining based on the map of the endometrial lining of the uterus of the patient, and using the control system to position a biopsy apparatus to obtain a biopsy in the specific area of interest.

16. A method as in claim 15, wherein the biopsy apparatus comprises a collector and plunger system.

17. A method as in claim 15, wherein the biopsy comprises at least one biopsy technique selected from an optical biopsy technique and a physical biopsy technique.

18. A method as in claim 1, further comprising:

providing an imaging sensor to control the timing of the obtaining of images image;

detecting changes in position of the omni-directional tip of the endoscope within the collapsed cavity formed by the uninsufflated uterus of the patient using a position sensor; and triggering the imaging sensor to obtain an image upon receiving a signal from the position sensor indicating that the omni-directional tip of the endoscope has moved a predetermined distance within the collapsed cavity formed by the uninsufflated uterus of the patient after a first image has been obtained.

19. A method as in claim 18, further comprising:

obtaining a plurality of additional images of the collapsed cavity formed by the uninsufflated uterus of the patient using the imaging device, wherein the omni-directional tip of the endoscope is moved in the collapsed cavity formed by the uninsufflated uterus of the patient between each of the additional images, the additional images each including distortion created by the imaging device, processing the additional images to remove at least a portion of the distortion in each of the images; and combining at least a portion of each of the additional images together with the at least a portion of the first image and the at least a portion of the second image.

20. The method of claim 1 further comprising inserting the omni-directional tip of the endoscope to the uterine fundus before capturing the series of images used to form the map of the endometrial lining of the uterus of the patient.

21. The method of claim 1, wherein the body portion is rigid.

22. The method of claim 1, wherein the body portion contains an illumination channel.

23. The method of claim 22, wherein the illumination channel is a ring of optic fibers surrounding the imaging channel.

24. The method of claim 22, further comprising illuminating the endometrial lining of the uninsufflated uterus of the patient by directing light from a tight source located outside the patient into the illumination channel.

25. A method of mapping the endometrial lining of an uninsufflated uterus of a patient, comprising:

attaching an image sensor to an imaging channel contained within a body portion of an endoscope having a distal end and a proximal end, where the imaging channel extends along an optical axis to an omni-directional tip located at the distal end of the body portion of the endoscope, where the omni-directional tip includes a rigid window that extends along a length of the body portion of the endoscope and around the circumference of the body portion of the endoscope and has a field of view projecting out from the rigid window that is capable of imaging a portion of the endometrium alongside the length of the body portion of the endoscope that includes the rigid window;

inserting the omni-directional tip of the endoscope into the collapsed cavity formed by the uninsufflated uterus of the patient so that the endometrial lining of the uninsufflated uterus becomes in contact with the rigid window of the omni-directional tip;

moving a portion of the endoscope that is outside the patient's body to move the omni-directional tip of the endoscope around the collapsed cavity formed by the uninsufflated uterus of the patient;

capturing images of portions of the endometrial lining extending around the circumference of the endoscope and in contact with the rigid window using the image sensor as the omni-directional tip moves around the collapsed cavity formed by the uninsufflated uterus of the patient, where the images include warping introduced due to the optics of the omni-directional tip that image light from the field of view of the window;

applying a transformation to each image to dewarp the image and produce anatomical images; and combining at least a portion of the processed images into at least one map of the endometrial lining of the uterus of the patient.

26. The method of claim 25, wherein:

the rigid window extends 360 degrees around the circumference of the omni-directional tip to create a 360 degree field of view around the optical axis;

the captured images include ring-like segments showing portions of the endometrial lining in contact with the rigid window in the 360 degree field of view on end to the optical axis of the imaging channel;

the transformation maps the ring-like segments to a rectangular anatomical image;

discarding portions of the rectangular anatomical images that are distorted; and combining the portions of the rectangular anatomical images to form at least one map of the endometrial lining of the uterus of the patient.

27. The method of claim 25, further comprising correcting for non-uniform illumination of the portions of the endometrial lining imaged through the window.

28. The method of claim 25 further comprising:

measuring the change in position of the endoscope as it moves around the collapsed cavity formed by the uninsufflated uterus of the patient;

wherein the combining at least a portion of the processed images into at least one map of the endometrial lining of the uterus of the patient further comprises using the measured change in position to register the portions of the processed images with respect to each other.

* * * * *